US006512005B2

(12) United States Patent
Bercovici et al.

(10) Patent No.: US 6,512,005 B2
(45) Date of Patent: Jan. 28, 2003

(54) PROCESS FOR SYNTHESIS OF PURE WARFARIN ACID, WARFARIN ALKALI METAL SALTS AND CORRESPONDING CLATHRATES

(75) Inventors: Sorin Bercovici, Kiriat Ono; Yuval Evron, Lower Galilee; Osvaldo Fuxman, Haifa; Mirela Jakoel, Kiriat Motzkin; Sbar Sasson, Rehovot; Konstantin Ulanenko, Natania, all of (IL)

(73) Assignee: Taro Pharmaceutical Industries, Ltd., Hawthorne, NY (US)

( * ) Notice: Subject to any disclaimer, the term of this patent is extended or adjusted under 35 U.S.C. 154(b) by 0 days.

(21) Appl. No.: 09/794,211

(22) Filed: Feb. 28, 2001

(65) Prior Publication Data

US 2002/0120155 A1 Aug. 29, 2002

(51) Int. Cl.$^7$ .................. A61K 31/35; C07D 311/02

(52) U.S. Cl. ...................... 514/457; 549/286

(58) Field of Search ............... 549/286; 574/457

(56) References Cited

U.S. PATENT DOCUMENTS

| | | | |
|---|---|---|---|
| 2,427,578 A | 9/1947 | Stahmann et al. | |
| 2,752,360 A | 6/1956 | Starr et al. | 260/343.2 |
| 2,765,321 A | 10/1956 | Schroeder et al. | 260/343.2 |
| 2,777,859 A | 1/1957 | Link et al. | 260/343.2 |
| 3,077,481 A | 2/1963 | Schroeder et al. | 260/343.2 |
| 3,192,232 A | 6/1965 | Schroeder et al. | 260/343.2 |
| 3,239,529 A | 3/1966 | Preis et al. | 260/284 |
| 3,246,013 A | 4/1966 | Weiner et al. | 260/343.2 |
| 4,113,744 A | 9/1978 | Badran | 260/343.2 |
| 4,818,297 A | 4/1989 | Holzmuüller et al. | 134/12 |
| 4,826,689 A | 5/1989 | Violanto | 424/489 |
| 5,686,631 A | 11/1997 | Li et al. | 549/286 |
| 5,696,274 A | 12/1997 | Uwaydah et al. | 549/285 |
| 5,856,525 A | 1/1999 | Li et al. | 549/286 |

FOREIGN PATENT DOCUMENTS

| | | |
|---|---|---|
| FR | 1397213 | 12/1963 |
| WO | WO 97/24347 | 7/1997 |

OTHER PUBLICATIONS

Ohnishi, "Structure–Activity Relationship between the Hydrophobicity of Alkali metal Salts of Warfarin [3–(α–Acetonyl–benzyl)–4–hydroxycoumarin] and the Effectiveness of the Taste Response to These Salts in Mice", Biosci. Biotech. Biochem., 59 (6), 995–1001. 1995.
Ivanov, "New Efficient Catalysts in the Synthesis of Warfarin and Acenocoumarol", Arch. Pharm (Weinheim), 1990, 323, pp. 521–522.
Bush et al, "High yield Synthesis of Warfarin and Its Phenolic Metablites: New Compounds", Journal of Pharmaceutical Sciences, vol. 72, No. 7, pp. 830–831, Jul. 1983.
Seidman et al, "Studies on 4–Hydroxycoumarins. X. Acylation of 3–(α–Phenyl–β–acetylethyl)–4–hydroxycoumarin", Journal of American Chemical Society, Nov. 1950, pp. 5193–5195.
Ikawa et al, "Studies on 4–Hydroxycoumarins. V. The Condensation of α, β–Unsaturated Ketones with 4–Hydroxycoumarin", Journal of American Chemical Society, 1944, pp. 902–906.
"Warfarin Sodium", Pharmaceutical Manufacturing Encyclopedia, 2$^{nd}$ Ed., vol. 2, 1988, pp. 1590–1591.
Hiskey et al, "Clathrates of Sodium Warfarin" Journal of Pharmaceutical Science, 1965, pp. 1298–1302.
12$^{th}$ Edition, 10174 "Warfarin", pp. 1715 (1996).
Kleemann & Engel, et al. "Pharmaceutical Substances" 3$^{rd}$ Ed (English), p. 2010 (1999).
Demir, Ayhan S., et al., "Enantioselective Synthesis of 4–Hydroxy–3–(3–Oxo–1–Phenyl Butyl)–2H–1–Benzopyran–2–One (Warfarin)," Turk. J. Chem., pp. 139–145 (1996).
Joshi, C.G., et al., "Studies in the Synthesis of Warfarin [3–a–Acetonylbenzyl)–4–hyroxycoumarin]," Indiana J. Technol., pp. 461–462 (1972).
Finn, Sidney Louis, "Thermogravimetric Analysis of Sodium Warfarin Isopropanol Clathrate (i:4:0)," A Thesis Submitted to the Graduate Faculty of the North Dakota State University of Agriculture and Applied Sciences, Jul. 1977.
Robinson, Andrea, et al., "The First Practical Asymmetric Synthesis of R and S–Warfarin," Tetrahedron Leters., vol. 37, No. 46, pp. 8321–8324 (1996).
Gao, Danchen, et al., "Use of Solution Calorimetry to Determine the Extent of Crystallinity of Drugs and Excipients," International Journal of Pharmaceutics, 151, pp. 183–192 (1997)..
Gao, Danchen, et al., "Physical Chemical Stability of Warfarin Sodium," AAPS Pharmaci, 2001, pp. 1–8 (Jan. 16, 2001).
Oözcan, Eyüp, et al., "The Factors Effecting the Reaction Efficiency in Warfarin Synthesis," Journal Marmara Univ. Fen Bilimleri Derg., vol. 6, pp. 155–67 (1989) (article and citation attached).
Yang, Tsang–Hsiung, et al., "Synthesis of Anticoagulants, Dicumarol And Warfarin," Tai–wan K'o Hseu, pp. 1–7 (1984).
Manolov, I., et al., Synthesis and Antimetastic Properties of 4–hydroxy–3(3–oxo–1–phenylbutyl)–2H–1–benzopyran–2–one (Warfarin), Farmatsiya(Sofia), pp. 1–6 (1990) (English abstract).
Xu, Xinyaun, "The Identification of Principal Components of Clathrate and Complex with Infrared Spectral Substraction Method," Chinese Journal of Pharmaceutical Analysis (China), vol. 17, pp. 87–89 (Mar. 1997) (English abstract).

Primary Examiner—Amelia Owens
(74) Attorney, Agent, or Firm—Venable; Michael A. Gollin; Keith G. Haddaway

(57) ABSTRACT

An improved procedure for the purification of warfarin acid. Sodium, potassium and lithium warfarin salts and the corresponding clathrates are prepared in high, pharnacopeial grade purity and good yields from the pure warfarin acid and the respective metal salt bases in suitable media.

42 Claims, No Drawings

PROCESS FOR SYNTHESIS OF PURE WARFARIN ACID, WARFARIN ALKALI METAL SALTS AND CORRESPONDING CLATHRATES

BACKGROUND OF THE INVENTION

1. Field of the Invention

The invention relates to a synthesis of pure warfarin acid and derivatives thereof. In particular, the invention relates to a commercially feasible, large scale process for purification of warfarin acid in high, pharmacopoeial grades of purity.

2. Background

Warfarin sodium, warfarin sodium 2-propanol clathrate, warfarin potassium and warfarin lithium 2-propanol clathrate are highly potent anticoagulants, generally administered orally and used extensively as active pharmaceutical ingredients (APIs). These compounds are also widely used as rodenticides in different dosages and formulations.

The commercial production of APIs preferably uses systems and processes capable of providing high quality, pure intermediates and products complying with pharmacopoeial requirements. Numerous procedures for the synthesis of warfarin acid, its salts and clathrates exist, but there is still a need by the pharmaceutical industry for methods of preparing these compounds in high quality as both intermediates and products and particularly for the preparation of high purity warfarin acid.

Warfarin acid and its alkali metal salts are coumarinic type derivatives having powerful anticoagulant properties. They are useful, established vitamin K related anticoagulant pharmaceuticals for the treatment of humans and animals. For example:

Warfarin sodium and its 2-propanol clathrate is marketed under various commercial names like Coumadin; Marevan; Prothromadin; Tintorane; Warfarin sodium; Warfilone; Waran.

Warfarin potassium salt is available under the name Athrombin K. These substances are also the active component in common rodenticide agents.

Warfarin acid, known chemically as racemic 4-hydroxy-3-(3-oxo-phenylbutyl)-2H-1 -benzopyran-2-one or 3-(-acetonylbenzyl)-4-hydroxycoumarin, is typically prepared by the Michael addition reaction of commercially available or in situ prepared 4-hydroxycoumarin to 4-phenyl-3-buten-2-one (benzalacetone). A wide range of conditions, for example, variations in solvents, variation of acidic and basic catalysts, varying temperatures, etc., have been used in synthetic procedures described in the literature. Although warafarin acid is a well known chemical entity, a simple, commercially feasible and direct preparation of warfarin acid in the pure state has not been significantly addressed.

Earlier purification methods described by Ikawa et al. (U.S. Pat. No. 2,427,578, see also, *J. Am. Chem. Soc.* 1944, 66, 902) or by Siedman et al. (*J. Am. Chem. Soc.* 1950, 72, 5193), as well as many others, recrystallize the crude acid from acetone-water mixtures.

U.S. Pat. No. 4,113,744 to Badran et al., describes a method for preparation of pure, microcrystalline warfarin acid by dissolution of the commercial impure acid into a special amine buffered-water system, filtration and reprecipitation of the pure, microcrystalline acid by pH readjustment of the filtrate.

Bush and Trage described a procedure for the preparation of pure warfarin acid, comprising ether extraction of the crude acid, back-extraction with dilute sodium hydroxide, filtration of the alkaline solution, and reprecipitation with 5 N HCl solution. (*J. of Pharm. Sci.* 1983, 72 (7), 830–831.) The pure acid is obtained by further recrystallization from acetone-water.

More recent references (for example, Ivanov et al., *Arch. Pharm* (Weinheim) 1990, 323, 521–522; Uwaydah et al. WO 97/24347) describe extraction/recrystallization procedures using glacial acetic acid or ethyl acetate.

Warfarin alkali salts, chemically known as 4-hydroxy-3-(3-oxo-phenylbutyl)2H-1-benzopyran-2-one alkali salts or 3-(-acetonylbenzyl)-4-hydroxycoumnarin sodium, potassium or lithium salts, are usually prepared by reacting warfarin acid with a molar equivalent or less of the respective alkali metal bases in aqueous medium, or with the metal alkoxides in lower alkyl alcohols.

U.S. Pat. No. 2,765,321 to Schroeder et al. describes a process of preparing crystalline warfarin sodium by reacting an aqueous sodium hydroxide solution with an excess of warfarin acid, followed by removal of the acid excess by addition of ethanol and filtration. The final warfarin sodium salt is obtained through a salting out procedure using lithium chloride addition into the ethanol-water solution of the warfarin sodium salt, cooling and recovering the precipitated warfarin sodium by filtration.

U.S. Pat. No. 2,777,859 to Link et al. describes a process of preparing an aqueous solution of warfarin alkali metal derivatives by adding an aqueous alkali metal hydroxide to an excess of water wet warfarin acid, warming and removing the excess of warfarin acid by filtration.

U.S. Pat. No. 3,077,481 to Schroeder et al. describes a process of purifying colored warfarin sodium by dissolving the amorphous salt in warm 2-propanol, cooling the resulting solution and recovering the crystalline warfarin sodium 2-propanol clathrate product.

In French Patent 1.397.213, Yates and Thomson describe an improved preparation of warfarin sodium by reacting a suspension of warfarin acid in an anhydrous lower alkyl alcohol with a solution containing a molar equivalent of sodium hydroxide dissolved in the same solvent. The crude product is isolated as a syrup upon solvent evaporation and must be further purified and subjected to thorough drying or lyophilization. The product is normally not of pharmaceutical quality. The warfarin sodium may be purified by dissolving in 2-propanol from which the crystalline clathrate is isolated by filtration. The 2-propanol trapped may be removed by evaporation to dryness in vacuo of the crystalline salt solutions in methanol, ethanol or acetone. Further purification is required in order to obtain a pharmaceutical grade substance.

U.S. Pat. No. 3,192,232 to Schroeder and Link describes a process for preparing warfarin sodium and warfarin potassium salts by reacting a slurry or warfarin acid in acetone-water with less than an equivalent of sodium hydroxide or potassium hydroxide in water at room temperature. The solution of the crude salt is purified by stirring with active charcoal and isolating of the salt by evaporation to dryness, spray drying, or drum drying.

Ohnishi et al. have described a method for preparing warfarin alkali metal salts by dissolving warfarin acid in an aqueous solution containing an equivalent amount of the respective alkali metal hydroxide (lithium, sodium, potassium, rubidium and cesium). Biosci. *Biotech. Biochem.* 1995, 59(6), 995–1006 (cf. CA 123: 105246 (1996)) The respective salts are isolated by lyophilization.

In a recent patent publication, WO 97/24347 (published Jul. 10, 1997), Uwaydah et al. describe a comprehensive process for warfarin alkali salts (sodium and potassium) and clathrate preparation starting from 2-hydroxyacetophenone and a carbonate ester. The hydroxycoumarin thus obtained is further reacted with benzalacetone in the presence of a phase transfer catalyst to give warfarin acid in a procedure similar to those of Ivanov (see reference above). The latter intermediate is further reacted with sodium or potassium hydroxide or carbonate, or preferably with sodium or potassium methoxide or ethoxide in anhydrous ethanol or 2-propanol to ultimately yield the desired product.

As can be seen from the description of existing preparations, there is a great deal of interest in this field, and a number of synthetic routes for the preparation of warfarin acid and its salts exist. However, the need remains for an economical, industrially feasible procedure to produce a high quality, pharmacopeial grade of warfarin acid and related salts.

SUMMARY OF THE INVENTION

Further objectives and advantages will become apparent from a consideration of the description, and nonlimiting examples described therein.

The present invention is a process for preparing pure warfarin acid from crude warfarin acid by suspending the crude acid in a water immiscible solvent, preferably toluene, extracting the acid into an aqueous solution of dilute base, separating the resulting aqueous phase and diluting it with a lower alkyl alcohol, for example, methanol, ethanol or, preferably, 2-propanol. Preferably, the aqueous solution is filtered before being diluted with the lower alkyl alcohol. The lower alkyl alcohol is preferably added to a concentration of about 50%. The solution is acidified to a pH of about 2 to 5 using a suitable acid, such as hydrochloric, sulfuric or phosphoric acid and the like. Sulfuric acid is preferred. The resulting suspension is stirred at a temperature of from about 20° C. to about 60° C., preferably about 40° C. to about 50° C., cooling suspension below room temperature, preferably to about 5° C. to about 10° C., filtering the pure warfarin acid and drying.

The crude warfarin acid for use in the purification is preferably prepared by hydrolyzing cyclocoumarol using about 2% to about 10% of an acidic catalyst which is preferably 4-toluene sulfonic acid, to a solution of cyclocoumarol in a mixture of a polar water miscible solvent and water at a temperature of from about room temperature to about the boiling point of the solvent. The reaction is preferably conducted in butanone or acetone containing about 35% to about 65% of water, preferably about 40% to about 50% water, and is most preferably conducting at reflux temperatures.

In another aspect, the invention is a method for preparing warfarin potassium by reacting pure warfarin acid with potassium carbonate in a non aqueous solvent, preferably 2-propanol. The solvent preferably contains between about 0.5% and about 5% of water by volume, and more preferably from about 1% to about 3% of water by volume. The molar ratio of potassium carbonate to warfarin acid is preferably between about 0.9 and about 2, and more preferably 0 between about 1.0 and about 1.3, to ensure yield and quality of the final product. The preparation of warfarin potassium is preferably conducted at a temperature of from about room temperature to about the boiling point of the solvent. More preferably, the reaction is carried out at reflux temperature. The reaction is typically complete in a time of from about 1 to about 5 hours, and more preferably is completed in from about 2 hours to about 3 hours. In a preferred embodiment, the solids remaining after the reaction is complete, which consist primarily of unreacted potassium carbonate, are removed by filtration. The pure warfarin potassium precipitates from the reaction mixture as a crystalline pure solid, which is collected by filtration.

In another aspect the invention is a process for preparing warfarin lithium 2-propanol clathrate comprising reacting pure warfarin acid with a solution of lithium 2-propoxide in anhydrous 2-propanol. Preferred parameters are otherwise identical to those for the preparation of warfarin potassium.

In yet another aspect, the invention is a process for preparing warfarin sodium comprising reacting pure warfarin acid with sodium carbonate in a water miscible polar solvent other than 2-propanol. Preferably, the water miscible polar solvent is acetone, ethanol, acetonitrile or butanone, and is most preferably butanone. The pure warfarin sodium is collected by solvent removal or addition of a low polarity solvent, for example, hexane, heptane or cycloheptane.

In yet another aspect, the invention is a method for making a pharmaceutical warfarin preparation from the pure warfarin acid prepared according to the invention, converting the pure warfarin acid to a pharmaceutically acceptable warfarin acid derivative such as warfarin potassium, warfarin sodium, warfarin lithium, and warfarin lithium 2-propanol clathrate, or other salts and clathrates, and preparing a pharmaceutical warfarin dosage form including the warfarin acid derivative. The dosage form may be, for example, tablets, capsules, geltabs, powders, granules, solutions and suspensions.

The present invention succeeds where previous efforts have failed by providing a convenient synthesis of pure warfarin acid. The invention is particularly advantageous in providing for the preparation of warfarin derivatives from the pure warfarin acid allowing use of the derivatives without additional purification.

This invention solves a previously unrecognized problem and provides a method for the preparation of pure warfarin acid enabling the production of higher quality warfarin derivatives without the need for additional purification.

This invention presents an improved synthesis of warfarin acid and its derivatives in a crowded and mature art by providing a method for preparing warfarin acid in a pure form not readily obtainable by use of existing methods without additional purification.

This invention provides advantages that were not previously appreciated such as the more efficient synthesis of high purity warfarin derivatives.

The invention provides an advantage in producing warfarin acid in the form of large crystals that are more easily filtered, facilitate ease of drying and shorten drying times.

This invention satisfies a long felt need for a convenient, industrially useful synthesis of pure warfarin acid. This pure warfarin acid of the invention is suitable for preparing warfarin sodium, warfarin potassium, warfarin lithium, and clathrates.

DETAILED DESCRIPTION OF THE INVENTION

In describing preferred embodiments of the present invention, specific terminology is employed for the sake of clarity. However, the invention is not intended to be limited to the specific terminology so selected. All references cited herein are incorporated by reference as if each had been individually incorporated by reference.

"Pure," as used herein, refers to a substance that meets at least one of the standards of the U.S. Pharmacopoeia (USP), British Pharmacopoeia, European Pharmacopoeia (Ph.Eur). EPCRS refers to the European Pharmacopoeial Commission of Reference Substances and USPRS refers to U.S. Pharmacopoeial Reference Standards. The EPCRS and USPRS provide reference standards for warfarin sodium and warfarin acid.

Non-limiting examples of suitable nonpolar solvents include aliphatic and aromatic hydrocarbons, for example, hexane, heptane, cyclohexane, toluene and benzene. Toluene is particularly preferred.

Non-limiting examples of water miscible solvents include lower molecular weight alcohols (methanol, ethanol, isopropanol, etc.), acetonitrile, ketones (acetone, methylethyl ketone, etc.), and ethers (tetrahydorfuran, 1,4-dioxane, etc.).

Extensive research has demonstrated that the purity of warfarin acid used to prepare derivatives has a critical effect on the quality of the final warfarin salts and their usefulness as APIs. Therefore, a fully reproducible, industrially feasible procedure for the preparation of pure warfarin acid as a key intermediate is presented.

The procedure for preparing pure warfarin acid according to the invention comprises the following:

1) Preparation of a cyclocoumarol derivative by the Michael addition reaction of 4-hydroxycoumarin to benzalacetone in methanol at reflux, using known procedures.

2) Preparation of the crude warfarin acid by acid catalyzed hydrolysis of the cyclocoumarol in a butanone-water or acetone-water system. A preferred acid catalyst is 4-toluene sulfonic acid. The acid concentration is preferably about 2% to about 10% and more preferably about 3% to about 6%. Less than 2% acid is generally inefficient, and greater than 10%–15% leads to increased impurities and may be uneconomical. The butanone or acetone contains about 30% to about 60%, preferably about 40% to about 50%, water. The reaction may be conducted at a temperature from about room temperature to the reflux temperature of the solvent. Preferably, the reaction is conducted at about reflux temperature. Although other methods of preparing crude warfarin acid may in principle be used, the inventors have found that the purification steps which follow are most effective when crude warfarin acid is prepared by this method.

3) Novel, improved preparation of pure warfarin acid by suspension of the crude acid in a low polarity, water immiscible solvent, dissolution and extraction of the warfarin acid into an aqueous alkaline phase as the warfarin salt, separation, and optionally filtration, of the aqueous alkaline solution followed by dilution with a lower alkyl alcohol, preferably above room temperature. The low polarity water immiscible solvent is preferably non-chlorinated and is most preferably toluene. The alkaline solution is preferably an aqueous solution of a dilute base, for example, sodium hydroxide. A preferred lower alkyl alcohol solvent is 2-propanol, although other lower alkyl alcohols, for example, methanol or ethanol, may be used. The pure, crystalline warfarin acid is preferably isolated by filtration of the precipitated substance. The acid used to precipitate the warfarin acid may be an aqueous acid selected from hydrochloric acid, sulfuric acid, phosphoric acid and the like. Sulfuric acid is preferred.

It has surprisingly been found that the conditions for dilution of the aqueous salt solution and precipitation of the purified warfarin acid are instrumental in obtaining high purity warfarin acid without the need for additional purification procedures which tend to be costly and time consuming. After separating and filtering the aqueous solution of warfarin acid salt, dilution of the aqueous solution with a lower alkyl alcohol, preferably at or above room temperature, is critical. Accordingly, prior to the addition of the acid, the solution is stirred, preferably at a temperature of from about 20° C. to about 60° C., more preferably from about 40° C. to about 50° C. The lower alkyl alcohol, preferably 2-propanol, is added at a temperature at or above room temperature. Although the amount of alcohol is not critical, the resultant solution preferably contains from about 30% to about 60% isopropanol, more preferably between about 40% and about 50% isopropanol, to prevent loss of the pure acid. The acid is then added to a pH of about 2–5 at or above room temperature. Precipitation at or above temperature is critical and results in the generation of warfarin acid with higher purity and larger crystals.

After addition of the acid, the suspension is stirred at or above room temperature. Precipitation is further facilitated by cooling the suspension to a temperature below room temperature, preferably from about 5° C. to about 10° C. The pure, crystalline warfarin acid is then isolated by filtration of the precipitated substance.

This invention also relates to procedures for preparing pure warfarin derivatives including salts and clathrates. Warfarin derivatives particularly include warfarin sodium, warfarin potassium and warfarin lithium 2-propanol clathrate, from the pure warfarin acid previously described. It will be appreciated that warfarin salts of other ions may be formed and clathrates incorporating solvents other than 2-propanol may be prepared according to the invention.

These procedures comprise the following:

1) Warfarin sodium is prepared by refluxing the pure warfarin acid with an excess of sodium carbonate in a polar solvent such as acetone or butanone, which may be either anhydrous or contain from about 1% to about 10% water. The unreacted sodium carbonate is preferably removed by filtration. The product is isolated by evaporating the solvent to dryness or by precipitating the salt by addition of a nonpolar solvent such as hexane, cyclohexane, heptane and the like, and filtering and drying the precipitate.

2) Warfarin potassium salt is prepared by refluxing the pure warfarin acid with an equivalent amount or an excess of potassium carbonate in 2-propanol. The 2-propanol may be anhydrous or may contain about 0.5% to about 10% water, preferably about 1% to about 3% water. The molar ratio of potassium carbonate to warfarin acid is between about 0.9 and about 2, and is preferably between about 1.0 and about 1.3. The reaction may be conducted at a temperature ranging from room temperature to the boiling point of the solvent for a time of from about 1 hour to about 5 hours. Preferably, the reaction is conducted at reflux temperature and the preferred reaction time is from about 2 hours to about 3 hours. The unreacted carbonate is removed by filtration. The warfarin potassium is precipitated and isolated as a pure crystalline solid by filtration and drying.

3) Warfarin lithium-2-propanol clathrate is prepared by reacting pure warfarin acid with a small excess of lithium-2-propoxide in 2-propanol (prepared in situ from lithium strips or rods). The product is isolated by cooling, precipitation, filtration and drying.

For the described processes, there are possible variations of some of the conditions which may provide somewhat different results. Some of the varying conditions that might be more preferable are varying time and temperatures, level of stirring, and reaction vessel characteristics. These may be further explored for any particular available equipment and for the respective final product desired. Varying processes to optimize conditions for a particular laboratory setting may be determined by routine experimentation. Such processes would be apparent to persons skilled in the art in light of the teachings of the present invention.

Warfarin derivatives prepared according to the present invention may be made into pharmaceutical dosage forms with appropriate pharmaceutically acceptable carriers or diluents. If appropriate, pharmaceutical dosage forms may be formulated into preparations including, but not limited to, solid, semi-solid, liquid, or gaseous forms, such as tablets, capsules, powders, granules, ointments, solutions, suppositories, injections, inhalants, and aerosols, in the usual ways for their respective route of administration. Methods known in the art can be utilized to prevent release or absorption of the warfarin derivative until it reaches the target organ or to ensure time-release of the composition. A pharmaceutically-acceptable form should be employed which does not ineffectuate the compositions of the present invention. In pharmaceutical dosage forms, the compositions may be used alone or in appropriate association, as well as in combination with, other pharmaceutically-active compounds.

To illustrate the invention and its particular usefulness, the following non-limiting examples are presented which exemplify the invention, but do not define its full scope:

EXAMPLES

Example 1

Preparation of Pure Warfarin Acid

The full, two step reaction and purification procedure, starting from cyclocoumarol methyl ether is hereinafter described:

A. Crude Warfarin Acid by Cyclocoumarol Hydrolysis

Cyclocoumarol methyl ether (1720 g, previously prepared in 72% yield by the known procedure, using 1.2 kg of benzalacetone, in methanol) was added to a solution of butanone (6.5 L) containing 4-toluene sulfonic acid monohydrate (170 g). Water (4 L) was added and the mixture stirred at reflux for about 4 hours.

The reaction solution was then concentrated to about half of its initial volume by azeotropic distillation of butanone/water, wherein the crude warfarin acid began to precipitate. The suspension was gradually cooled and the crude, wet warfarin acid was obtained by filtration and washed with cold butanone and water.

Yield: 1320–1390 g (80–85% from cyclocoumarol) on a dry basis. (The wet substance contained about 15–25% moisture and was directly used into the next step.)

Physical properties of the crude warfarin acid were identical to an authentic sample (warfarin acid USP standard).

B. Pure Warfarin Acid from Crude Warfarin Acid

The crude (wet) acid from example 1 was added to toluene (5.5 L) and the mixture stirred at room temperature until a homogeneous suspension was achieved. A solution of 5% sodium hydroxide (about 4 L) was then added to the stirred suspension until a basic pH was reached and an almost clear two-phase solution was obtained. The stirring was stopped and the layers allowed to separate. The lower aqueous phase was filtered by suction and the upper organic phase discarded.

The aqueous filtrate was returned to the vessel and gently warmed to 40–50° C. 2 Propanol (4 L) was added and the solution stirred for about ½ hour while maintaining the temperature.

Sulfuric acid (20% solution in water) was then added slowly in portions to the warm, stirred solution, until a constant acidic pH was achieved. A total of about 1.5–2 L of sulfuric acid solution was needed, while the pure warfarin acid precipitated as a bright-white crystalline solid.

The thick suspension was stirred for an additional 1 hour, then cooled to below 10° C. for another hour.

The cold suspension was filtered, thoroughly washed with demineralized water and finally with cold 2-propanol.

The pure warfarin was obtained as a white crystalline powder upon drying in a vacuum oven for 8–10 hours.

Yield: 1250–1300 g (90–95% from the crude acid) M.P.: 159.6–161.2° C. (lit. 161° C.) Clarity and color: clear and almost colorless. Color by UV absorption at 385 nm (of the 10% w/v solution in 1N NaOH): <0.30 AU. Related substances (TLC): none detected.

Physical properties of the product were identical to warfarin acid USPRS.

Example 2

Preparation of Warfarin Sodium

A three-neck, round bottom flask provided with mechanical stirrer, thermometer and reflux/distillation condenser was successively charged with pure warfarin acid, (308 g, 1 mole), odium carbonate (Merck, art. 106398) (106 g, 1 mole) and butanone (MEK, CP, 3100 ml).

The mixture was heated to reflux with stirring for 8 hours, then cooled to room temperature and filtered.

The clear solution was returned to the flask and the solvent volume reduced to about ⅓ of the initial volume by distillation.

Heptane (3100 ml) was slowly added in portions to the residue in the flask and the mixture stirred at room temperature for an additional 4 hours.

Warfarin sodium was isolated as a white powder by suction filtration, washing and drying to constant weight in a vacuum oven at 35–40° C. and 1 mm Hg. Yield: 298 g(90%); Clarity of the alkaline solution: clear and colorless (complies with Ph.Eur and USP). Color (phenolic ketones) by UV absorption: <0.1 AU (complies with Ph.Eur and USP). pH of 1% aqueous solution: 7.86 (complies with Ph.Eur and USP). Related substances (by TLC): not more than 0.1% (complies with Ph.Eur). Identification (IR): identical with the warfarin sodium EPCR standard.

Example 3

Preparation of Warfarin Sodium

As per Example 2 above but using pure warfarin acid (0.1 mole) and hexane (300 ml) instead of heptane.

Yield: 29 g (88%); Clarity, color (by UV) and related substances as in example 2 above. pH: 7.8; Analysis: Identical to EPCR standard.

Example 4

Preparation of Warfarin Potassium

A mixture of pure warfarin acid (31 g, 0.1 mole) and potassium carbonate (99%) (10.4 g, 0.75 mole) in 2-propanol (CP grade, 160 ml) was stirred at 20–25° C. for 2 hours, in a suitable glass flask under a nitrogen atmosphere.

The unclear solution was filtered using suction and the filtrate was cooled to below 5° C. for 4–6 hours.

The precipitated solid was carefully filtered by nitrogen pressure, washed with cold 2-propanol and dried in a vacuum oven (40–50° C., 10 mm Hg) for 6–8 hours to give pure warfarin potassium as a white, hygroscopic, crystalline solid.

Yield: 24.3 g (70%); Identification (by IR vs. warfarin acid standard): complies; Potassium test: positive; $^1$H-NMR test: pattern practically identical to warfarin sodium-EPCRS. Thermal analysis (by DSC): no solvent release endotherm observed (in contrast to warfarin sodium 2-propanol clathrate).

Both $^1$H-NMR and DSC data strongly suggested that warfarin potassium does not form clathrates with 2-propanol.

Example 5

Preparation of Warfarin Lithium 2-Propanol Clathrate

A solution of lithium 2-propoxide in 2-propanol was prepared by reacting lithium rods, (0.42 g, 0.06 at.-g) with excess 2-propanol (CP anhydrous, 10 ml). This solution was added dropwise to a stirred suspension of pure warfarin acid (15.4 g, 0.05 mole) in 2-propanol (60 ml), under a nitrogen atmosphere.

The clear solution was stirred at room temperature for two hours until a solid partially precipitated.

The suspension was further cooled to about 0° C. for 4 hours, the white solid precipitate was carefully filtered under nitrogen pressure, washed with cold 2-propanol and dried in a vacuum oven (40–50° C., 10 mm Hg) for 8–12 hours to give the pure warfarin lithium 2-propanol clathrate as a white, crystalline powder.

Yield: 15 g (80.2%); Identification (by IR, vs. warfarin acid standard): complies; $^1$H-NMR test: pattern practically identical to an authentic warfarin sodium clathrate sample, but the integral of the protons relative to the respective methyl groups suggested an equimolar content of IPA in clathrate. IPA content (by GC): 15.1%; Thermal analysis (by DSC): typical endotherm, similar to those observed with an authentic warfarin sodium 2-propanol clathrate sample appeared around 160° C., suggesting the existence of a clathrate.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A process for preparing pure warfarin acid comprising the steps of:
   (a) providing crude warfarin acid suspended in a water immiscible solvent,
   (b) combining the water immiscible solvent with an alkaline aqueous phase,
   (c) extracting the crude warfarin acid into the alkaline aqueous phase as a warfarin salt,
   (d) separating the aqueous phase from the water immiscible solvent,
   (e) diluting the aqueous phase with a lower alkyl alcohol,
   (f) acidifying the diluted aqueous/lower alkyl alcohol phase with an aqueous acid to give a suspension of pure warfarin acid.

2. The process according to claim 1, further comprising filtering the aqueous phase after separating the aqueous phase from the water immiscible solvent.

3. The process according to claim 1, wherein the diluted aqueous phase is acidified at a temperature above room temperature.

4. The process according to claim 1, further comprising cooling the suspension of pure warfarin acid.

5. The process according to claim 1, further comprising filtering pure warfarin acid.

6. The process according to claim 1, wherein the water immiscible solvent is toluene.

7. The process according to claim 1, wherein the alkaline aqueous phase is dilute sodium hydroxide.

8. The process according to claim 1, wherein the aqueous phase is heated to a temperature of from about 20° C. to about 60° C. before diluting with the lower alkyl alcohol.

9. The process according to claim 1, wherein the aqueous phase is heated to a temperature of from about 40° C. to about 50° C. before diluting with the lower alkyl alcohol.

10. The process of claim 1, wherein the lower alkyl alcohol is added to a concentration of about 50%.

11. The process according to claim 1, wherein the lower alkyl alcohol is selected from the group consisting of methanol, ethanol and 2-propanol.

12. The process according to claim 1, wherein the lower alkyl alcohol is 2-propanol.

13. The process according to claim 1, wherein the aqueous acid is selected from the group consisting of hydrochloric acid, sulfuric acid and phosphoric acid.

14. The process according to claim 1, wherein the aqueous acid is sulfuric acid.

15. The process according to claim 4, wherein the suspension of pure warfarin acid is cooled below room temperature.

16. The process according to claim 4, wherein the suspension of pure warfarin acid is cooled to a temperature of between about 5° C. and about 10° C.

17. The process according to claim 1, wherein the crude warfarin acid is prepared by a process comprising the step of:
   adding an acid catalyst to a solution of cyclocoumarol in a water miscible solvent containing up to about 50% water at a temperature from about room temperature to about the boiling point of the solvent.

18. The process according to claim 17, wherein the acidic catalyst is 4-toluenesulfonic acid.

19. The process according to claim 17, wherein the water miscible solvent is butanone or acetone.

20. A process for the preparation of pure warfarin potassium or clathrate thereof, comprising the steps of: reacting pure warfarin acid prepared according to the process of claim 1 with a potassium carbonate in a nonaqueous solvent, and
   removing unreacted metal carbonate.

21. The process according to claim 20, wherein the nonaqueous solvent contains from about 0.5% to about 10% water.

22. The process according to claim 20, wherein the nonaqueous solvent contains from about 0.5% to about 5% water by volume.

23. The process according to claim 20, wherein the nonaqueous solvent contains from about 1% to about 3% water by volume.

24. The process according to claim 20, wherein the ratio of molar equivalents of potassium carbonate to warfarin acid is from about 0.9 to about 2.

25. The process according to claim 20, wherein the ratio of molar equivalents of potassium carbonate to warfarin acid is from about 1.0 to about 1.3.

26. The process according to claim 20, further comprising the step of precipitating the pure warfarin potassium.

27. The process according to claim 20, wherein the nonaqueous solvent is 2-propanol.

28. A process for the preparation of pure warfarin lithium 2-propanol clathrate comprising the step of: reacting pure warfarin acid prepared according to claim 1 with lithium 2-propoxide in anhydrous 2-propanol.

29. Pure warfarin acid prepared by the steps of:
(a) providing crude warfarin acid suspended in a water immiscible solvent,
(b) combining the suspension with an alkaline aqueous phase,
(c) extracting warfarin acid into the aqueous phase as a warfarin salt,
(d) separating the aqueous phase,
(e) diluting the aqueous phase with a lower alkyl alcohol,
(f) acidifying the diluted aqueous/lower alkyl alcohol phase using an aqueous acid to give a suspension of pure warfarin acid.

30. The pure warfarin acid of claim 29, wherein the preparation further comprises: filtering the aqueous phase before diluting with the lower alkyl alcohol.

31. The pure warfarin acid of claim 29, wherein the aqueous phase is heated to a temperature at or above room temperature before diluting with the lower alkyl alcohol.

32. The pure warfarin acid of claim 29, wherein the preparation further comprises cooling the suspension of pure warfarin acid.

33. The pure warfarin acid of claim 29, wherein the preparation further comprises filtering pure warfarin acid.

34. A process for preparing pure warfarin acid comprising:
step for preparing a suspension of crude warfarin acid in a water immiscible solvent,
step for isolating warfarin salt thereof in an alkaline aqueous phase,
step for separating the aqueous phase,
step for achieving a dilution of the aqueous phase with a lower alkyl alcohol,
step for producing a suspension of pure warfarin acid by acidifying the diluted aqueous/lower alkyl alcohol phase with an aqueous acid, and,
step for obtaining pure warfarin acid from the suspension.

35. The process according to claim 34, wherein the step for obtaining pure warfarin acid from the suspension comprises a step for obtaining a cooled suspension.

36. The process according to claim 34, further comprising a step for filtering the aqueous phase before the step for achieving a dilution of the aqueous phase.

37. Pure warfarin acid prepared by the steps of:
(a) suspending crude warfarin acid in toluene,
(b) extracting the crude warfarin acid into dilute aqueous sodium hydroxide as a warfarin salt,
(c) separating the aqueous solution,
(d) heating the aqueous solution to a temperature of from about 20° C. to about 60° C.,
(e) diluting the aqueous phase with 2-propanol to a concentration of from about 40% to about 50% 2-propanol while maintaining the temperature at from about 20° C. to about 60° C., and
(f) acidifying the 2-propanol/aqueous solution with sulfuric acid to a constant pH at a temperature of from about 20° C. to about 60° C. to give a suspension of pure warfarin acid.

38. The pure warfarin acid of claim 37, wherein the preparation further comprises the steps of:
(g) cooling the suspension to a temperature of less than about 10° C., and
(h) filtering pure warfarin acid.

39. A method for making a pharmaceutical warfarin preparation comprising preparing pure warfarin acid from crude warfarin acid by a process comprising the steps of
(a) providing crude warfarin acid suspended in a water immiscible solvent,
(b) combining the water immiscible solvent with an alkaline aqueous phase,
(c) extracting the crude warfarin acid into the alkaline aqueous phase as a warfarin salt,
(d) separating the aqueous phase from the water immiscible solvent,
(e) diluting the aqueous phase with a lower alkyl alcohol, and
(f) acidifying the diluted aqueous/lower alkyl alcohol phase with an aqueous acid to give a suspension of pure warfarin acid,
converting the pure warfarin acid to a pharmaceutically acceptable warfarin derivative, and preparing a pharmaceutical warfarin dosage form comprising said warfarin derivative, wherein the dosage form is not warfarin sodium 2-propanol clathrate tablets.

40. The method of claim 39, wherein the pharmaceutically acceptable warfarin derivative is selected from the group consisting of warfarin salts and clathrates.

41. The method of claim 39, wherein the dosage form is selected from the group consisting of tablets, capsules, geltabs, powders, granules, solutions and suspensions.

42. A method for making a pharmaceutical warfarin preparation comprising preparing pure warfarin acid from crude warfarin acid by a process comprising the steps of
(a) providing crude warfarin acid suspended in a water immiscible solvent,
(b) combining the water immiscible solvent with an alkaline aqueous phase,
(c) extracting the crude warfarin acid into the alkaline aqueous phase as a warfarin salt,
(d) separating the aqueous phase from the water immiscible solvent,
(e) diluting the aqueous phase with a lower alkyl alcohol, and
(f) acidifying the diluted aqueous/lower alkyl alcohol phase with an aqueous acid to give a suspension of pure warfarin acid,
converting the pure warfarin acid to a pharmaceutically acceptable warfarin derivative selected from the group consisting of warfarin potassium, warfarin sodium, warfarin lithium, and warfarin lithium 2-propanol clathrate, and
preparing a pharmaceutical warfarin dosage form comprising said warfarin derivative.

* * * * *